(12) United States Patent
Peters

(10) Patent No.: US 6,520,972 B2
(45) Date of Patent: Feb. 18, 2003

(54) SURGICAL CLIP APPLIER

(76) Inventor: Stephen F. Peters, 13700 Kelly Rd., Hickory Corners, MI (US) 49060

( * ) Notice: Subject to any disclaimer, the term of this patent is extended or adjusted under 35 U.S.C. 154(b) by 0 days.

(21) Appl. No.: 09/775,462

(22) Filed: Feb. 2, 2001

(65) Prior Publication Data

US 2001/0047178 A1 Nov. 29, 2001

Related U.S. Application Data

(60) Provisional application No. 60/180,354, filed on Feb. 4, 2000.

(51) Int. Cl.$^7$ .............................................. A61B 17/10
(52) U.S. Cl. ........................ 606/143; 606/143; 606/142
(58) Field of Search .................................. 606/142, 143

(56) References Cited

U.S. PATENT DOCUMENTS

| | | | |
|---|---|---|---|
| 5,163,945 A | 11/1992 | Ortiz et al. .................. | 606/142 |
| 5,199,566 A | 4/1993 | Ortiz et al. .................. | 206/339 |
| 5,300,081 A | 4/1994 | Young et al. ................ | 606/143 |
| 5,514,149 A | 5/1996 | Green et al. ................ | 606/158 |
| 5,527,318 A | 6/1996 | McGarry ..................... | 606/139 |
| 5,591,178 A | 1/1997 | Green et al. ................ | 606/143 |
| RE35,525 E | 6/1997 | Stefanchik et al. .......... | 606/143 |
| 5,643,291 A | 7/1997 | Pier et al. ................... | 606/143 |
| 5,695,502 A | 12/1997 | Pier et al. ................... | 606/143 |
| 5,700,270 A | 12/1997 | Peyser et al. ............... | 606/142 |
| 5,720,756 A | 2/1998 | Green et al. ................ | 606/143 |
| 5,725,538 A | 3/1998 | Green et al. ................ | 606/143 |
| 5,755,726 A | 5/1998 | Pratt et al. ................... | 606/143 |
| 5,772,673 A | 6/1998 | Cuny et al. .................. | 606/143 |
| 5,833,696 A | 11/1998 | Whitfield et al. ........... | 606/143 |
| 5,868,761 A | 2/1999 | Nicholas et al. ............. | 606/143 |
| 5,938,667 A | 8/1999 | Peyser et al. ............... | 606/142 |
| RE36,720 E | 5/2000 | Green et al. ................ | 606/151 |
| 6,059,799 A | 5/2000 | Aranyi et al. ............... | 606/143 |
| 6,109,500 A | 8/2000 | Alli et al. ................. | 227/175.2 |

*Primary Examiner*—Gary Jackson
(74) *Attorney, Agent, or Firm*—Howard & Howard

(57) ABSTRACT

A surgical clip applier for application of surgical clips to body tissue is disclosed. The clip applier includes an elongated housing having proximate and distal ends. This housing also defines a feed surface for the surgical clips. The clip applier also includes first and second jaws extending from the distal end of the housing. The jaws open and close to apply the surgical clips to the body tissue of the patient. A driver is disposed within the housing to advance the surgical clips from the feed surface to the jaws. The clip applier of the present invention incorporates a backing surface extending from the distal end of the housing and extending along the jaws. Accordingly, the backing surface bears against the jaws by constantly applying a force such that the housing is always pre-loaded against the jaws. As such, the jaws are maintained in proper alignment with the feed surface and the surgical clips can be advanced from the feed surface to the jaws without a misfeed.

25 Claims, 3 Drawing Sheets

SURGICAL CLIP APPLIER

RELATED APPLICATIONS

This patent application claims priority to and all advantages of United States Provisional Patent Application No. 60/180,354 which was filed on Feb. 4, 2000.

BACKGROUND OF THE INVENTION

1) Technical Field

The subject invention generally relates to a clip application assembly for application of a surgical clip to body tissue. More specifically, the subject invention relates to a clip application assembly that introduces a backing surface that extends along a portion of a jaw apparatus to pre-load the housing against the jaw apparatus to maintain proper alignment within the clip application assembly.

2) Description of the Prior Art

Clip application assemblies for application of surgical clips are well known in the surgical art. The clip application assemblies of the prior art include an elongated housing having proximate and distal ends. The housings of the prior art assemblies also define a clip feed surface. These assemblies also include a jaw apparatus extending from the distal end of the housing, and a clip driver within the housing to advance the surgical clip from the clip feed surface to the jaw apparatus where the surgical clip is applied to body tissue.

The clip application assemblies of the prior art are deficient in that the jaw apparatus at the distal end of the housing is permitted to move or to float freely. That is, in the prior art, there is no component in the clip application assemblies that actively bears against the jaw apparatus to pre-load the jaw apparatus and prevent movement or floating of the jaw apparatus. It is generally understood that the clip feed surface and the jaw apparatus must be aligned as the surgical clip is advance to the jaw apparatus. Proper alignment ensures proper application of the surgical clip to the body tissue. Because the jaw apparatuses in the prior art assemblies are not pre-loaded and are therefore permitted to move, the surgical clips in these assemblies are commonly misfed into the jaw apparatus from the clip feed surface. The misfeed of the surgical clip into the jaw apparatus results in either a jam of the surgical clip within the clip application assembly, or results in improper application of the surgical clip to the body tissue. It is understood throughout the industry that these two results are inefficient in terms of the time required to correct the jam and also in terms of patient safety when the surgical clip is misapplied.

Due to the inefficiencies identified above with respect to the clip application assemblies of the prior art, it is desirable to implement a novel clip application assembly that includes a backing surface extending from the distal end of the housing and along a portion of the jaw apparatus that bears against and pre-loads the jaw apparatus to maintain the jaw apparatus in alignment with the clip feed surface such that the surgical clip can be properly advanced from the clip feed surface to the jaw apparatus. As such, surgical time and patient safety are optimized as the jaw apparatus is pre-loaded and the surgical clip cannot be misfed into the jaw apparatus since the jaw apparatus is always in alignment with the clip feed surface.

SUMMARY OF THE INVENTION AND ADVANTAGES

A clip application assembly is disclosed. The clip application assembly of the subject invention applies a surgical clip or surgical clips to body tissue of a patient. The clip application assembly includes an elongated housing having proximate and distal ends. The housing defines a clip feed surface that is positioned adjacent the distal end. The clip application assembly also includes a jaw apparatus that extends from the distal end of the housing and included at least one jaw tip. Preferably, the jaw apparatus includes first and second legs. A clip driver is disposed within the housing. The clip driver advances the surgical clips from the clip feed surface to the jaw apparatus where the clip is then applied to the body tissue.

The clip application assembly further includes a backing surface that extends from the distal end of the housing and along a portion of the jaw apparatus. In such a position, the backing surface bears against the portion of the jaw apparatus and also pre-loads, or applies a constant force onto the jaw apparatus, in order to maintain the jaw apparatus in proper alignment with the clip feed surface. In other words, the housing is always preloaded against the jaw apparatus. As such, the surgical clips can be properly advanced from the clip feed surface to the jaw apparatus without a misfeed and the surgical clip can be applied to the body tissue properly and without a jam in the clip application assembly.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5 is a perspective view of a surgical clip utilized by the clip application assembly of the subject invention.

DETAILED DESCRIPTION OF THE PREFERRED EMBODIMENT

Figure 1:
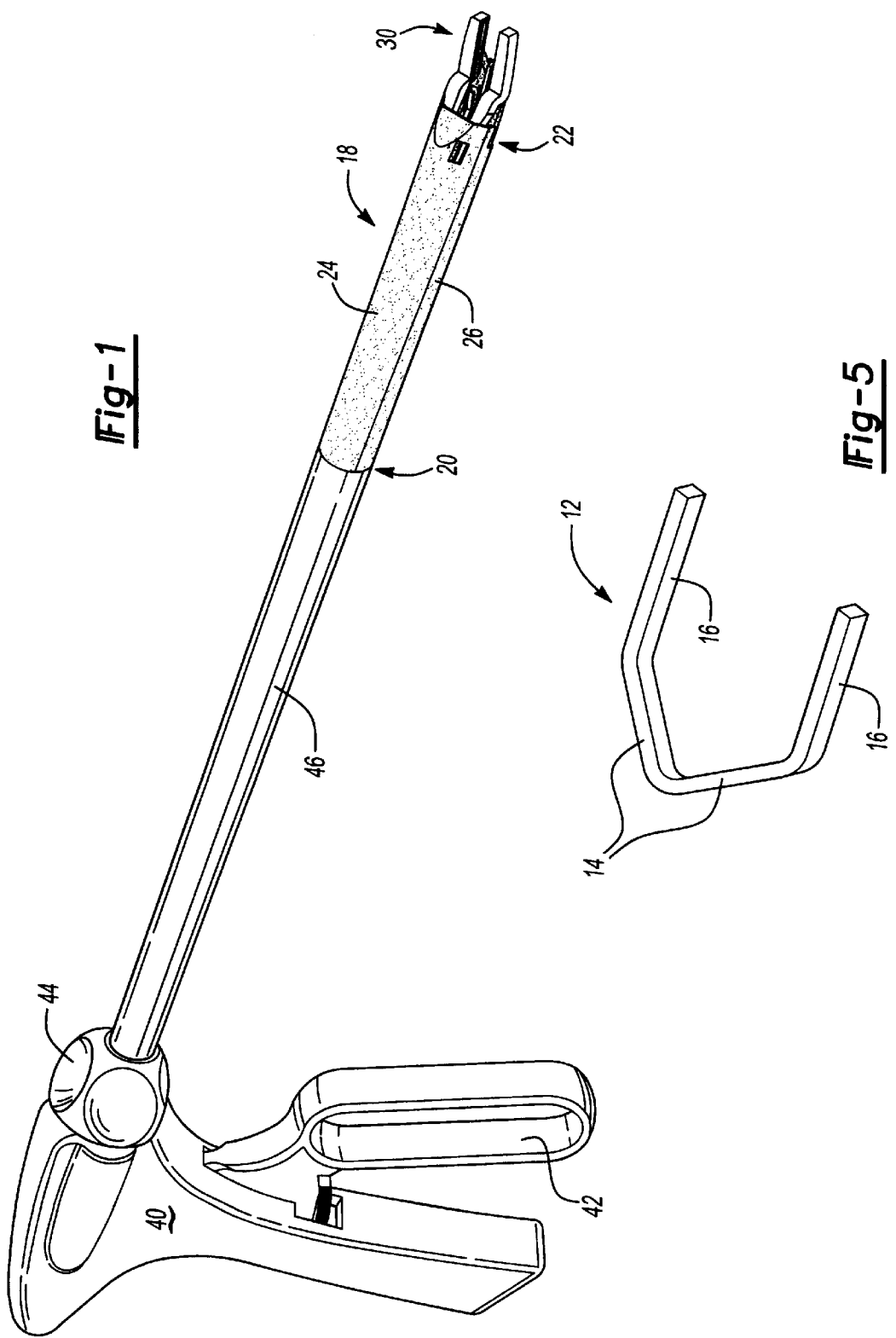
FIG. 1 is a perspective view of a clip application assembly.

Referring to the Figures, wherein like numerals indicate like or corresponding parts throughout the several views, a clip application assembly is generally shown at 10. The clip application assembly 10 is also referred to in the art as a surgical clip applier 10 and will be referenced as such in the following description. The clip applier 10 applies a surgical clip 12 (shown exclusively in FIG. 5) to body tissue of a patient. Of course, it is to be understood that although the clip applier 10 is described at times in terms of application of a single surgical clip 12, the clip applier 10 can also apply a plurality of surgical clips to the body tissue of the patient. The clip 12 of the preferred embodiment is of the shape disclosed in FIG. 5 and includes a clip base 14 and clip legs 16.

Referring primarily to FIG. 1, the clip applier 10 includes an elongated housing 18, or shaft, having proximate 20 and distal 22 ends. Preferably, the housing 18 is made from injection-molded polycarbonate. The housing 18 further includes a top half 24 and a bottom half 26. Although not required, the top and bottom halves 24, 26 of the housing 18 are preferably snap-fit together. The housing 18 defines a clip feed surface 28 (shown best in FIG. 3) adjacent its distal end 22. As shown in the Figures, the clip feed surface 28 includes first and second feed branches, not numbered in the Figures. It is to be understood that the surgical clips 12 are stored within the housing 18, preferably within a cartridge, near the clip feed surface 28.

Figure 2:
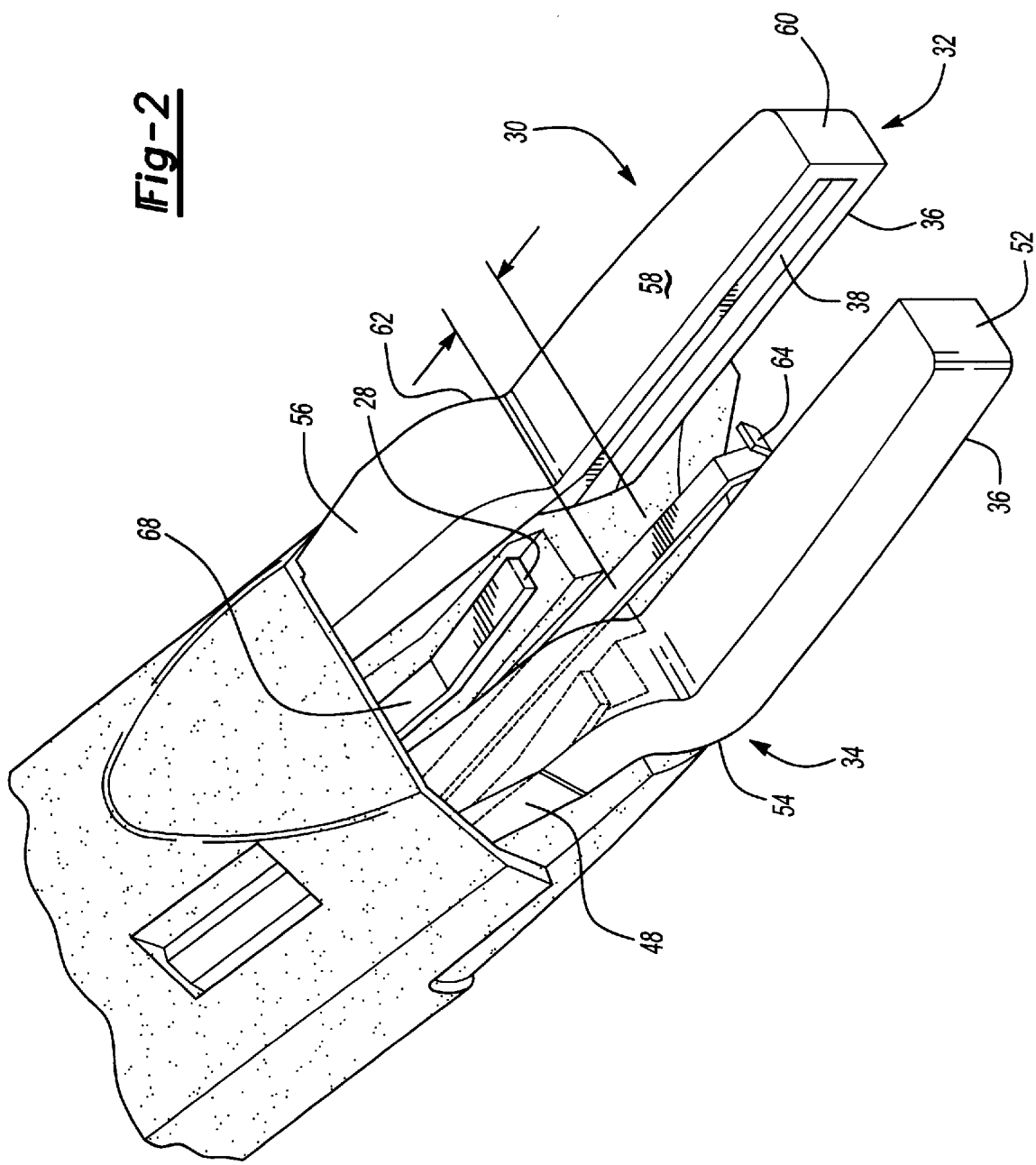
FIG. 2 is an enlarged perspective view of the clip application assembly illustrating a jaw apparatus and a backing surface bearing against the jaw apparatus.

Referring now to FIG. 2, the clip applier 10 further includes a jaw apparatus 30 including at least one jaw tip 32 and at least one jaw shoulder 34. The jaw apparatus 30 opens and closes for application of the surgical clips 12 to the body tissue of the patient. Although the jaw shoulder 34 may be angled, the jaw shoulder 34 of the preferred embodiment is curved. This will be described further below. The jaw apparatus 30 extends outwardly at a particular angle from the distal end 22 of the housing 18. As shown in the Figures, the jaw apparatus 30 extends outwardly and upwardly from the distal end 22 of the housing 18. As such, the jaw apparatus 30 can be described to include an underside 36. However, because the clip applier 10 is rotatable, which is discussed below, upward extension of the jaw apparatus 30 from the housing 18 is used only for descriptive purposes and is not critical. The jaw apparatus 30 further includes at least one clip track 38 or clip groove. Preferably, the subject invention includes two clip tracks 38. The clip track 38 receives the surgical clips 12 from the clip feed surface 28. The surgical clips 12 are disposed in the clip track 38 as the jaw apparatus 30 opens and closes to apply the surgical clip 12 to the body tissue.

Referring back to FIG. 1, the clip applier 10 of the subject invention is utilized in combination with a handle 40 and a trigger 42. The trigger 42, which can be of any type without varying the scope of the subject invention, is disposed on the handle 40 assists in advancing the surgical clip 12 from the clip feed surface 28 to the jaw apparatus 30. As appreciated by those skilled in the art, the handle 40 and the trigger 42 are rotatable to through a rotating mechanism 44 relative to the housing 18 of the clip applier 10. Further, a support shaft 46 may optionally be incorporated between the handle 40 and the housing 18 for mounting between the clip applier 10 and the handle 40. If the support shaft 46 is included, then the proximate end 20 of the housing 18 is mounted to the support shaft 46 for connection with the handle 40 as is shown in FIG. 1. As such, the clip applier 10 of the subject invention can be replaced after a certain number of surgical clips 12 are expended, and the handle 40, the trigger 42, and the support shaft 46 can be refused.

Preferably, the jaw apparatus 30 includes first and second legs that are more specifically discussed below. However, it is to be understood that the jaw apparatus 30 of the subject invention can include any number of legs without varying the scope of the subject invention. The jaw apparatus 30 of the preferred embodiment more specifically includes a first proximate leg 48 and a first distal leg 50. A first jaw tip 52 is disposed on the first distal leg 50 of the jaw apparatus 30, and a first jaw shoulder 54 is defined between the first proximate and distal legs, 48 and 50, respectively. The preferred embodiment also includes a second proximate leg 56 and a second distal leg 58. As second jaw tip 60 is disposed on the second distal leg 58 of the jaw apparatus 30, and a second jaw shoulder 62 is defined between the second proximate and distal legs, 56 and 58, respectively. Preferably, both the first and second jaw shoulders, 54 and 62, respectively, are curved.

The clip applier 10 also includes a clip driver 64, also known in the art as a clip pusher, disposed within the housing 18 to advance the surgical clips 12 from the clip feed surface 28 to the jaw apparatus 30. The housing 18 also defines a guide track 66 or channel that is centered within the housing 18 and that is disposed between the first and second feed branches of the clip feed surface 28. Thus, the guide track 66 keeps the clip driver 64 centered as it advances the surgical clips 12 from the clip feed surface 28 to the jaw apparatus 30. The subject invention also incorporates clip guide fingers 68 which are utilized to maintain pressure on the surgical clips 12 in each of the feed branches of the clip feed surface 28 as the surgical clips 12 are advance to the jaw apparatus 30. As appreciated, the trigger 42 is actuated, i.e., pulled, to actuate the clip driver 64 and advance the surgical clips 12 to the jaw apparatus 30.

Figure 3:
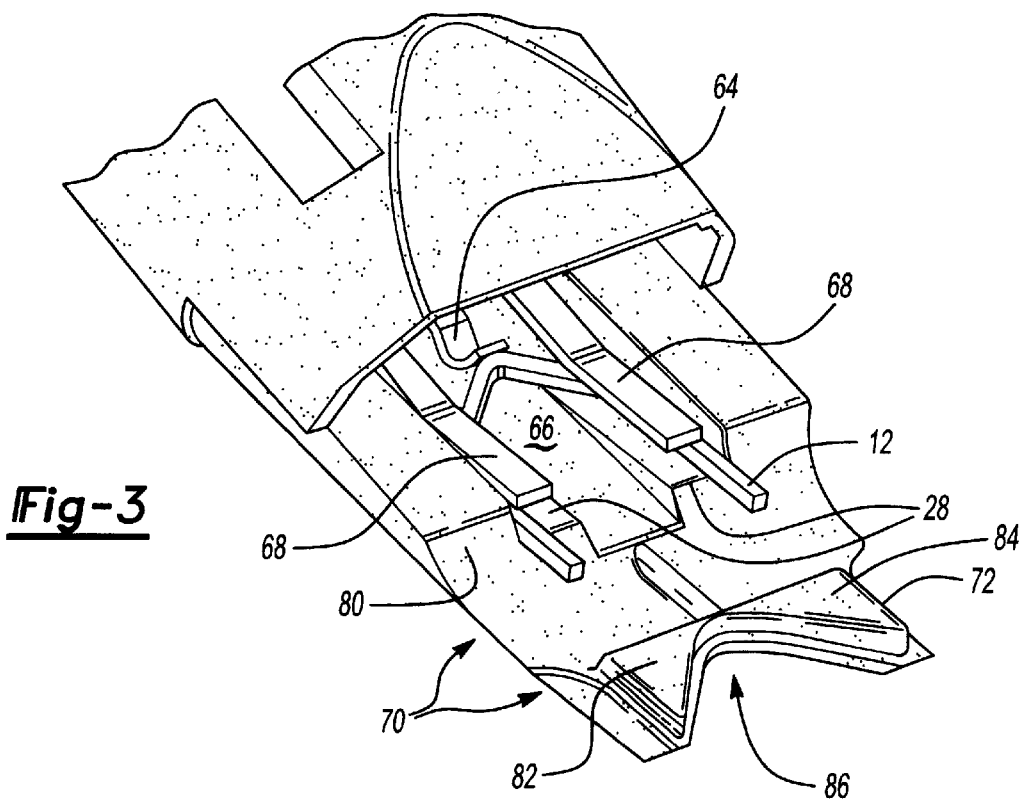
FIG. 3 is an enlarged perspective view of the clip application assembly without the jaw apparatus and illustrating, in significant detail, the backing surface.

Referring to FIG. 3, the subject invention incorporates a backing surface 70 that extends from the distal end 22 of the housing 18 and along a portion, or a length, of the jaw apparatus 30. More specifically, the backing surface 70 extends from the distal end 22 of the housing 18 at the bottom half 26 of the housing 18. The backing surface 70 bears against the portion of the jaw apparatus 30, specifically the underside 36 of the jaw apparatus 30, by applying a constant force to the jaw apparatus 30. As such, the backing surface 70 actively and continuously pre-loads the jaw apparatus 30 thereby preventing the jaw apparatus 30 from moving, i.e., floating, and maintaining the jaw apparatus 30 in alignment with the clip feed surface 28. Throughout the description in the subject application, whenever the terminology discussing pre-loading the jaw apparatus 30 is utilized, such terminology is intended to indicate that the backing surface 70 bears against the portion of the jaw apparatus 30 such that the housing 18 is always pre-loaded against the jaw apparatus 30. The backing surface 70 aligns the clip track 38 in the jaw apparatus 30 with the clip feed surface 28. As discussed above, when the clip applier 10 is in proper alignment, the surgical clip 12 can be properly advanced from the clip feed surface 28 to the clip track 38 of the jaw apparatus 30.

Figure 4:
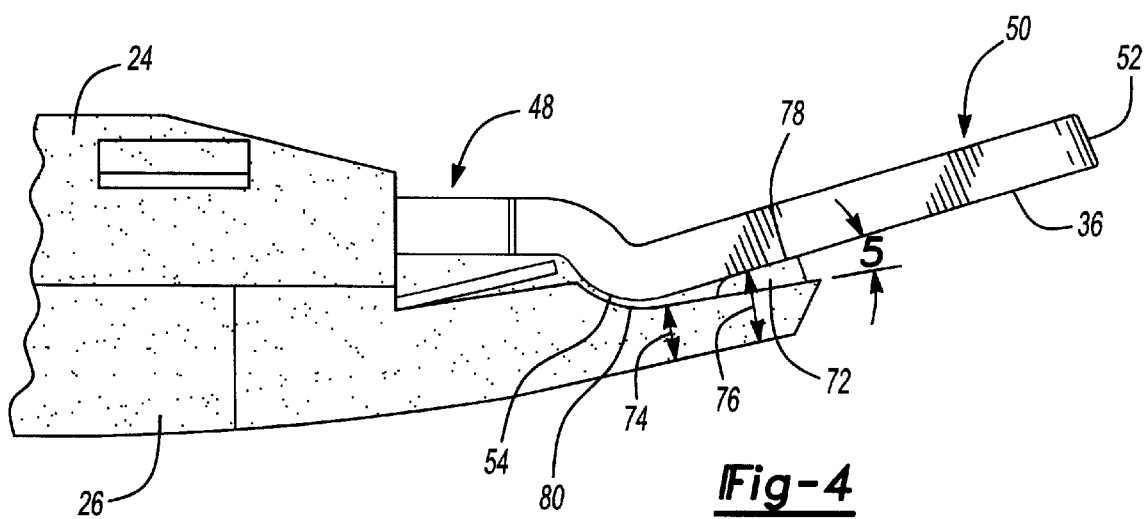
FIG. 4 is a side view of the clip application assembly illustrating the backing surface.

Referring to FIG. 3, the backing surface 70 includes a raised abutment surface 72, also termed a pad. Preferably, the raised abutment surface 72 is a direct extension of the backing surface 70 such that the raised abutment surface 72 is an integral part. The raised abutment surface 72 projects from the backing surface 70 toward the jaw apparatus 30 in order to pre-load the jaw apparatus 30. As shown best in FIG. 4, the raised abutment surface 72 establishes a varied thickness to the backing surface 70 in order to effectively bear against the jaw apparatus 30. More specifically, the varied thickness can be described as a first thickness 74 and a second thickness 76, and as shown in FIG. 4, the second thickness 76 which is nearest the jaw tip 32 is greater than the first thickness 74 which is nearest the clip feed surface 28. The raised abutment surface 72 includes a top facing 78 having a particular slope S. The slope S of the top facing 78 increases outwardly toward the jaw tip 32 such that it is the top facing 78 of the raised abutment surface 72 that bears against the portion of the jaw apparatus 30 to pre-load the jaw apparatus 30, Although it is apparent that the value of the slope S of the top facing 78 is not critical, it is critical that the slope S of the top facing 78 equal or exceed the angle at which the jaw apparatus 30 extends from the housing 18.

The backing surface 70 further includes a contoured portion 80 that is contoured around the first and second jaw shoulders, 54 and 62, respectively, such that the backing surface 70 does not contact the jaw shoulders, 54 and 62, respectively. The contoured portion 80 enables the backing surface 70 to bear against the portion of the jaw apparatus 30 after the jaw shoulders, 54 and 62, respectively, more toward the first and second jaw tips, 52 and 60, respectively. If, as in the preferred embodiment, the jaw shoulders, 54 and 62, respectively, are curved, then the contoured portion 80 is curved in a complimentary fashion around the curved jaw shoulders, 54 and 62, respectively, such that the backing surface 70 and the jaw shoulders, 54 and 62, respectively, do not contact one another. However, the contoured portion 80 may be angular in the event that the jaw shoulders, 54 and 62, respectively, are not curved so long as the backing surface 70 and the jaw shoulders, 54 and 62, respectively, do not contact.

In terms of the first and second distal legs, 50 and 58, respectively, of the jaw apparatus 30, the raised abutment surface 72 projects from the backing surface 70 to directly pre-load the first and second distal legs, 50 and 58, respectively. To accomplish this, the raised abutment surface 72 includes first 82 and second 84 stanchions. The first stanchion 82 of the raised abutment surface 72 pre-loads the first distal leg 50 of the jaw apparatus 30, and the second stanchion 84 of the raised abutment surface 72 pre-loads the second distal leg 58 of the jaw apparatus 30.

Finally, the backing surface 70 also defines a groove 86. The groove 86 is disposed between the first and second stanchions, 82 and 84, respectively, and in the preferred embodiment the groove 86 is centered. The groove 86 appropriately receives the body tissue during application of the surgical clip 12.

The pre-loading only requires that tolerances be such that the raised abutment surface 72 constantly applies some pressure to the jaw apparatus 30. The jaw apparatus 30 is typically constructed of a metal material, which receives the pre-load from the backing surface 70 of the housing 18 without adversely affecting an orientation of the clip track 38 in the jaw apparatus 30. In this way, the height of the raised abutment surface 72 can vary within a certain "window of opportunity" without affecting the alignment of the clip track 38 with the clip feed surface 28. With the use of the backing surface 70, including the raised abutment surface 72, the height of the raised abutment surface 72 only has to be within a tolerance of ±0.010. Previously, the positional tolerance of the clip track 38 was ±0.010 with the positional tolerance of the clip feed surface 28 being ±0.015 for a sum of tolerances equaling ±0.025. As a result, the subject invention improves the accuracy of the alignment of the clip feed surface 28 with the clip track 38 in the jaw apparatus 30 by about 160%.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A clip application assembly for application of a surgical clip to body tissue, said assembly comprising:
   an elongated housing having proximate and distal ends, said housing defining a clip feed surface adjacent said distal end;
   a jaw apparatus extending from said distal end of said housing and including at least one jaw tip;
   a clip driver disposed within said housing for advancing the surgical clip from said clip feed surface to said jaw apparatus; and
   a backing surface extending from said distal end of said housing and bearing against a portion of said jaw apparatus to contact and pre-load said jaw apparatus thereby maintaining said jaw apparatus in alignment with said clip feed surface such that the surgical clip can be properly advanced from said clip feed surface to said jaw apparatus.

2. A clip application assembly for application of a surgical clip to body tissue, said assembly comprising:
   an elongated housing having proximate and distal ends, said housing defining a clip feed surface adjacent said distal end;
   a jaw apparatus extending from said distal end of said housing and including at least one jaw tip;
   a clip driver disposed within said housing for advancing the surgical clip from said clip feed surface to said jaw apparatus; and
   a backing surface extending from said distal end of said housing and bearing against a portion of said jaw apparatus to contact and pre-load said jaw apparatus thereby maintaining said jaw apparatus in alignment with said clip feed surface such that the surgical clip can be properly advanced from said clip feed surface to said jaw apparatus,
   wherein said backing surface includes a raised abutment surface projecting from said backing surface toward said jaw apparatus to provide said contacting and said preloading of said jaw apparatus.

3. An assembly as set forth in claim 2 wherein said raised abutment surface establishes a varied thickness to said backing surface such that said backing surface bears against said portion to pre-load said jaw apparatus.

4. An assembly as set forth in claim 3 wherein said varied thickness of said backing surface includes a first thickness nearest said clip feed surface and a second thickness nearest said at least one jaw tip with said second thickness greater than said first thickness.

5. An assembly as set forth in claim 2 wherein said jaw apparatus extends from said distal end of said housing at an angle and said raised abutment surface includes a top facing having a slope, said slope of said top facing increasing outwardly toward said at least one jaw tip such that said top facing bears against said portion to pre-load said jaw apparatus.

6. A clip application assembly for application of a surgical clip to body tissue, said assembly comprising:
   an elongated housing having proximate and distal ends, said housing defining a clip feed surface adjacent said distal end;
   a jaw apparatus extending from said distal end of said housing and including at least one jaw tip and at least one jaw shoulder between said distal end of said housing and said at least one jaw tip;
   a clip driver disposed within said housing for advancing the surgical clip from said clip feed surface to said jaw apparatus; and
   a backing surface extending from said distal end of said housing and bearing against a portion of said jaw apparatus to contact and preload said jaw apparatus thereby maintaining said jaw apparatus in alignment with said clip feed surface such that the surgical clip can be properly advanced from said clip feed surface to said jaw apparatus,
   wherein said backing surface includes a contoured portion contoured around said jaw shoulder such that said backing surface does not contact said jaw shoulder and bears against said portion of said jaw apparatus after said jaw shoulder toward said at least one jaw tip.

7. An assembly as set forth in claim 6 wherein said at least one jaw shoulder is curved and said contoured portion is contoured around said curved jaw shoulder.

8. An assembly as set forth in claim 1 wherein said jaw apparatus further includes a first proximate leg and a first distal leg having a first jaw tip and a first jaw shoulder defined between said first proximate and distal legs, and a second proximate leg and a second distal leg having a second jaw tip and a second jaw shoulder defined between said second proximate and distal legs.

9. An assembly as set forth in claim 8 wherein said backing surface includes a raised abutment surface projecting from said backing surface toward said first and second distal legs of said jaw apparatus to pre-load said first and second distal legs.

10. An assembly as set forth in claim 9 wherein said raised abutment surface further includes first and second stanchions, said first stanchion of said raised abutment surface pre-loading said first distal leg and said second stanchion of said raised abutment surface pre-loading said second distal leg.

11. An assembly as set forth in claim 10 wherein said backing surface further includes a contoured portion contoured around said first and second jaw shoulders such that said backing surface does not contact said first jaw shoulder and bears against said portion of said jaw apparatus after said first jaw shoulder toward said first jaw tip and such that said backing surface does not contact said second jaw shoulder and bears against said portion of said jaw apparatus after said second jaw shoulder toward said second jaw tip.

12. An assembly as set forth in claim 1 wherein said housing further includes a top half and a bottom half, said backing surface extending from said distal end of said housing at said bottom half to pre-load said jaw apparatus.

13. An assembly as set forth in claim 1 wherein said jaw apparatus further includes at least one clip track adapted to receive the surgical clip from said clip feed surface, said backing surface extending along said portion and bearing against said portion to pre-load said jaw apparatus thereby maintaining said clip track of said jaw apparatus in alignment with said clip feed surface.

14. An assembly as set forth in claim 1 wherein said housing further defines a guide track for said clip driver disposed between first and second branches of said clip feed surface to keep said clip driver centered.

15. An assembly as set forth in claim 1 wherein said jaw apparatus extends upwardly from said distal end of said housing.

16. An assembly as set forth in claim 15 wherein said backing surface extends from said distal end of said housing along an underside of said jaw apparatus and bears against said underside to pre-load said jaw apparatus.

17. An assembly as set forth in claim 1 in combination with a handle and a trigger disposed on said handle for actuating said clip driver to advance the surgical clip from said clip feed surface to said jaw apparatus.

18. An assembly as set forth in claim 17 wherein said handle and said trigger are rotatable relative to said housing.

19. An assembly as set forth in claim 17 further including a support shaft disposed between said handle and said housing.

20. An assembly as set forth in claim 19 wherein said proximate end of said housing is mounted to said support shaft for connection with said handle.

21. An assembly as set forth in claim 10 wherein said backing surface defines a groove disposed between said first and second stanchions for receiving the body tissue during application of the surgical clip.

22. A clip application assembly comprising:

a surgical clip for application to body tissue;

an elongated housing having proximate and distal ends, said housing defining a clip feed surface adjacent said distal end;

a jaw apparatus extending from said distal end of said housing and including at least one jaw tip;

a clip driver disposed within said housing for advancing said surgical clip from said clip feed surface to said jaw apparatus; and a backing surface extending from said distal end of said housing and bearing against a portion of said jaw apparatus to contact and pre-load said jaw apparatus thereby maintaining said jaw apparatus in alignment with said clip feed surface such that said surgical clip can be properly advanced from said clip feed surface to said jaw apparatus.

23. A clip application assembly for application of a surgical clip to body tissue, said assembly comprising:

an elongated housing having proximate and distal ends, said housing defining a clip feed surface adjacent said distal end;

a jaw apparatus extending from said distal end of said housing and including at least one jaw tip;

a clip driver disposed within said housing for advancing the surgical clip from said clip feed surface to said jaw apparatus; and a backing surface extending from said distal end of said housing and bearing against a portion of said jaw apparatus to contact said jaw apparatus adjacent said at least one jaw tip and to pre-load said jaw apparatus thereby maintaining said jaw apparatus in alignment with said clip feed surface such that the surgical clip can be properly advanced from said clip feed surface to said jaw apparatus.

24. An assembly as set forth in claim 23 wherein said jaw apparatus further includes at least one jaw shoulder, and said backing surface bears against said portion of said jaw apparatus between said jaw shoulder and said at least one jaw tip.

25. An assembly as set forth in claim 23 wherein said backing surface includes a raised abutment surface projecting from said backing surface toward said jaw apparatus adjacent said at least one jaw tip to pre-load said jaw apparatus.

* * * * *